United States Patent
Fukasawa et al.

(10) Patent No.: US 10,610,422 B2
(45) Date of Patent: Apr. 7, 2020

(54) DISPOSABLE WEARING ARTICLE

(71) Applicant: Unicharm Corporation, Shikokuchuo-shi, Ehime (JP)

(72) Inventors: Jun Fukasawa, Kanonji (JP); Toshiyasu Yoshioka, Kanonji (JP); Noriko Nagase, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 54 days.

(21) Appl. No.: 15/563,049

(22) PCT Filed: May 18, 2015

(86) PCT No.: PCT/JP2015/064203
§ 371 (c)(1),
(2) Date: Sep. 29, 2017

(87) PCT Pub. No.: WO2016/174779
PCT Pub. Date: Nov. 3, 2016

(65) Prior Publication Data
US 2018/0369027 A1    Dec. 27, 2018

(30) Foreign Application Priority Data
Apr. 28, 2015 (JP) ................ 2015-092402

(51) Int. Cl.
*A61F 13/494* (2006.01)
*A61F 13/49* (2006.01)
*A61F 13/496* (2006.01)

(52) U.S. Cl.
CPC ........ *A61F 13/49426* (2013.01); *A61F 13/49* (2013.01); *A61F 13/496* (2013.01);
(Continued)

(58) Field of Classification Search
CPC ................ A61F 13/49426; A61F 13/49; A61F 13/49011; A61F 13/49466;
(Continued)

(56) References Cited

U.S. PATENT DOCUMENTS

| | | | |
|---|---|---|---|
| 2013/0079742 A1* | 3/2013 | Kuwano | A61F 13/49011 604/385.3 |
| 2013/0203580 A1 | 8/2013 | Lenser et al. | |

(Continued)

FOREIGN PATENT DOCUMENTS

| | | |
|---|---|---|
| JP | 2009-61046 A | 3/2009 |
| JP | 2009-240639 A | 10/2009 |

(Continued)

OTHER PUBLICATIONS

International Search Report for PCT/JP2015/064203 dated Jul. 14, 2015.
(Continued)

*Primary Examiner* — Tatyana Zalukaeva
*Assistant Examiner* — Gabriella E Burnette
(74) *Attorney, Agent, or Firm* — Hauptman Ham, LLP

(57) ABSTRACT

Provided is a wearing article that can prevent the folding of a waist panel. In a disposable wearing article that includes a waist panel for forming first and second waist regions, a liquid absorbent structure that extends from a crotch region to the first and rear waist regions and includes a liquid absorbent core, a waist opening, and a pair of leg openings, and at least in the first waist region out of the first and second waist regions, the liquid absorbent structure includes an end portion that extends from the end edge of the liquid absorbent core to the side of the waist opening, and the outer end edge of the end portion extends to the edge of the waist opening.

6 Claims, 9 Drawing Sheets

(52) U.S. Cl.
  CPC .. *A61F 13/49011* (2013.01); *A61F 13/49466* (2013.01); *A61F 13/49473* (2013.01); *A61F 2013/4948* (2013.01); *A61F 2013/49493* (2013.01)

(58) Field of Classification Search
  CPC .............. A61F 13/49473; A61F 13/496; A61F 2013/4948; A61F 2013/49493
  See application file for complete search history.

(56) References Cited

U.S. PATENT DOCUMENTS

2015/0366724 A1   12/2015  Fukuzawa et al.
2017/0290721 A1*  10/2017  Morimoto ......... A61F 13/49011

FOREIGN PATENT DOCUMENTS

| JP | 2010-246586 A | 11/2010 |
| JP | 2014-150909 A | 8/2014 |
| JP | 2015-505509 A | 2/2015 |
| WO | 2014/122980 A1 | 8/2014 |

OTHER PUBLICATIONS

Office Action in JP Application No. 2015-092402, dated Jul. 7, 2015.
Office Action in JP Application No. 2015-092402, dated Dec. 1, 2015.
Decision to Grant a Patent in JP Application No. 2015-092402, dated Mar. 8, 2016.

* cited by examiner

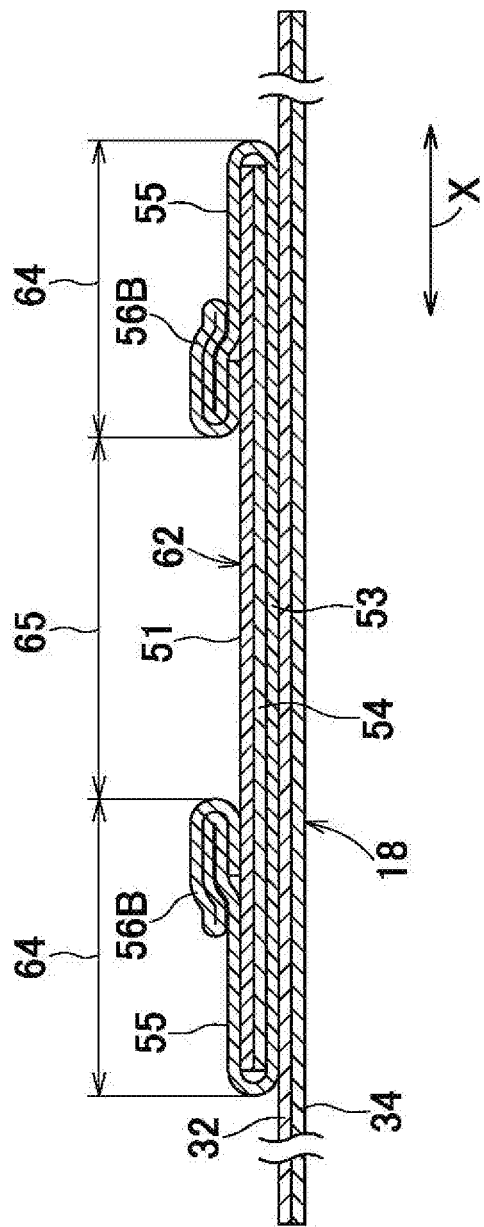

DISPOSABLE WEARING ARTICLE

RELATED APPLICATIONS

The present application is a National Phase of International Application Number PCT/JP2015/064203, filed May 18, 2015, which claims priority to Japanese Application Number 2015-092402, filed Apr. 28, 2015.

TECHNICAL FIELD

The present invention relates to a disposable wearing article.

BACKGROUND

Conventionally, disposable wearing articles are known including a waist panel defining front and rear waist regions, a liquid absorbent structure defining a crotch region, a waist opening, and a pair of leg openings. For example, in Patent Literature 1, the wearing article including the waist panel and the liquid absorbent structure is disclosed, and both end edges of the liquid absorbent structure are spaced apart from the waist opening.

CITATION LIST

Patent Literature

PTL 1: Japanese Unexamined Patent Application Publication No. 2009-240639 A

SUMMARY

Technical Problem

In such a wearing article, when it is put on a wearer in a state of lying down on a bed, a putting-on operation is easily made without trouble of engaging tape fasteners and fitting the wearing article to the wearer's body, compared with open-type wearing articles in which the front and rear waist regions are coupled by means of the tape fasteners.

However, in the wearing article of Patent Literature 1, the stiffness of sheet members constituting the wearing article is low in a section extending outboard the end edges of the liquid absorbent structure, so that the waist panel is prone to be folded in the section when the article is put on the wearer's body. When the folding occurs in the vicinity of end edges of a liquid absorbent core, a gap between the wearer's body and the wearing article are left, and body exudates may leak through the gap. When the wearer lies down on the bed, one of the rear or front waist regions is positioned between the wearer's body and the bed, which is hard for a wearer or caretaker to visually recognize the waist region, and the wearing article is worn in a state that the folding goes unnoticed, and the leakage of body exudates may occur through the gap.

It is an object of the present invention to provide a wearing article that can prevent the folding of a waist panel, as an improvement of conventional technologies.

Advantageous Effects of Invention

The present invention to solve the abovementioned problems is directed to improve a disposable wearing article includes a longitudinal direction and a lateral direction, a first waist region which is one of front and rear waist regions, a second waist region which is the other of the front and rear waist regions, a crotch region extending between the first and second waist regions, a waist panel defining the first and second waist regions, a liquid absorbent structure extending across the crotch region to the first and second waist regions and containing a liquid absorbent core, a waist opening, and a pair of leg openings.

The present invention is featured in the wearing article that at least in the first waist region out of the first and second waist regions, the liquid absorbent structure includes an end portion extending from an end edge of the liquid absorbent core to a side of the waist opening, and an outer end edge of the end portion extends to an edge of the waist opening.

According to one of the other embodiments of the present invention, at least in the first waist region out of the first and second waist regions, a waist opening edge of the waist panel approximately aligns with the outer end edge of the liquid absorbent structure in a plan view.

According to one of the other embodiments of the present invention, the end portion of the liquid absorbent structure has equal folding stiffness in the longitudinal direction ranging from the end edge of the liquid absorbent core to the edge of the waist opening.

According to one of the other embodiments of the present invention, the end portion of the liquid absorbent structure includes lateral edge portions spaced apart from each other in the lateral direction and a central portion between the lateral edge portions, and the lateral edge portions have high folding stiffness in the longitudinal direction, compared with the central portion.

According to one of the other embodiments of the present invention, at least in an area overlapped with the end portion of the liquid absorbent structure in a plan view, the folding stiffness of a sheet member constituting the waist panel in the longitudinal direction is uniform.

According to one of the other embodiments of the present invention, in an area overlapped with the end portion of the liquid absorbent structure in a plan view, the waist panel is contractible in the lateral direction.

According to one of the other embodiments of the present invention, the waist panel includes a plurality of string-like or strand-like waist elastics extending in the lateral direction, and in the region overlapped with the end portion of the liquid absorbent structure in a plan view, spaced-apart dimensions of the waist elastics adjacent to each other in the longitudinal direction are equal.

According to one of the other embodiments of the present invention, the liquid absorbent structure includes a pair of leakage-barrier cuffs positioned on lateral sides in the lateral direction and on a skin facing surface side of the liquid absorbent core, and the pair of leakage-barrier cuffs includes a fixation end portion extending from the end edge of the liquid absorbent core to an edge of the waist opening in the first waist region.

According to one of the other embodiments of the present invention, the liquid absorbent structure includes a cover sheet for the liquid absorbent core, and the cover sheet extends to the edge of the waist opening in the first waist region.

Solution to Problem

With the disposable wearing article according to the present invention, the outer end edge of the liquid absorbent structure extends to the edge of the waist opening, so that the waist panel is not folded at a section where the outer end edge is positioned, thereby preventing the leakage of body exudates.

BRIEF DESCRIPTION OF DRAWINGS

The drawings show specific embodiments of the present invention including optional and preferred embodiments as well as essential features of the invention.

FIG. 5 is a schematic cross-sectional view taken along line V-V of FIG. 2.

DESCRIPTION OF EMBODIMENTS

First Embodiment

Figure 1:
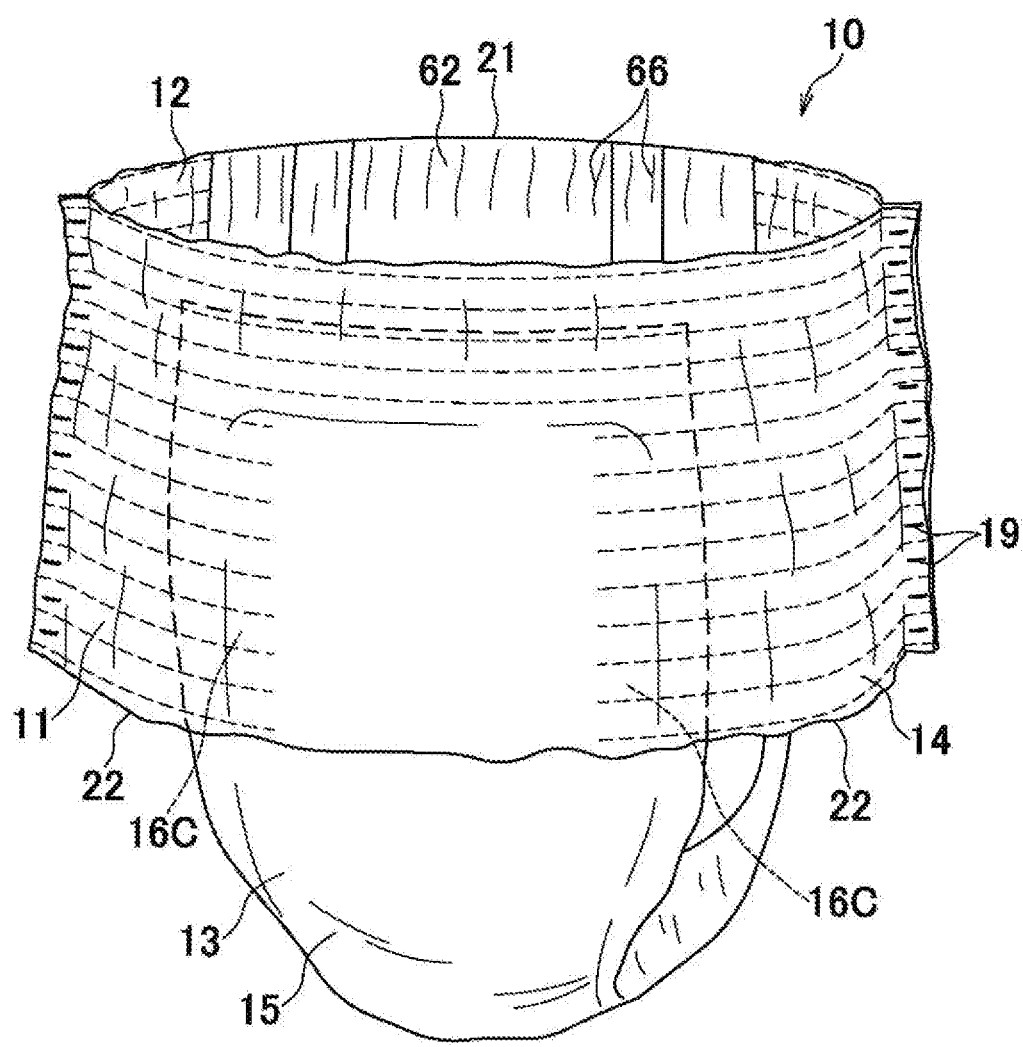
FIG. 1 is a perspective view of a disposable diaper, shown as one example of a disposable wearing article according to the present invention.

With reference to FIGS. 1 to 5, a disposable diaper 10 as one example of a disposable wearing article according to the present invention includes a longitudinal direction Y, a lateral direction X orthogonal to the longitudinal direction Y, a skin facing surface, a non-skin facing surface on the side opposite to the skin facing surface, a front waist region (a first waist region or a second waist region) 11, a rear waist region 12 (the second waist region or the first waist region) 12, a crotch region 13 extending between the front and rear waist regions 11, 12, an annular waist panel 14 defining the front and rear waist regions 11, 12, and a liquid absorbent structure 15 extending across the crotch region 13 to the front and rear waist regions 11, 12 and containing a liquid absorbent core 16. In each diagram in which the diaper 10 is unfolded, each elastic described later is in a state of being stretched against a contractile force. The diaper 10 has a longitudinal axis P dividing the dimension of the lateral direction X thereof and a lateral axis Q dividing the dimension of the longitudinal direction Y thereof.

<Waist Panel>

The waist panel 14 includes a front waist panel 17 defining the front waist region 11, and a rear waist panel 18 defining the rear waist region 12. The front and rear waist panels 17, 18 respectively has a rectangular shape defined by inner end edges 17*a*, 18*a* and outer end edges (waist opening edges) 17*b*, 18*b* extending in the lateral direction X and spaced apart from and opposite to each other in the longitudinal direction Y, and lateral edges 17*c*, 18*c* extending in the longitudinal direction Y between the inner and outer end edges 17*a*, 17*b*, 18*a*, 18*b*. The lateral edge 17*c* of the front waist panel 17 and the lateral edge 18*c* of the rear waist panel 18 opposing to each other are overlapped with each other and coupled with known means, for example, various thermal welding means such as thermal embossing/debossing and sonic treatment, on side seams 19 continually arranged in the longitudinal direction Y, and whereby a waist opening 21 and a pair of leg openings 22 are defined.

Figure 2:
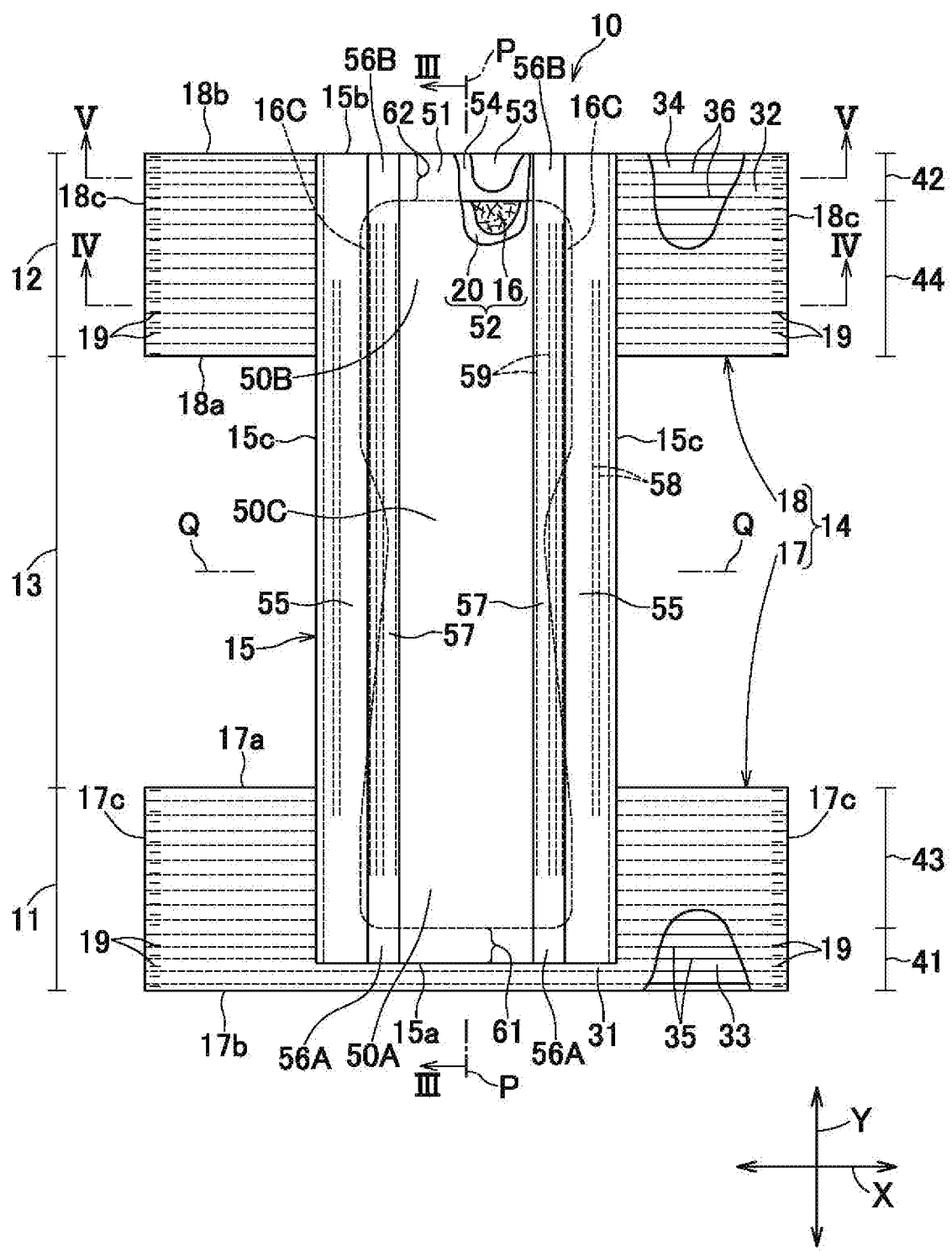
FIG. 2 is a partially broken expanded plan view of the diaper expanded in longitudinal and lateral directions when each elastic is extended to the maximum (to the extent that gathers disappear by the contraction action of the elastic).
Figure 3:
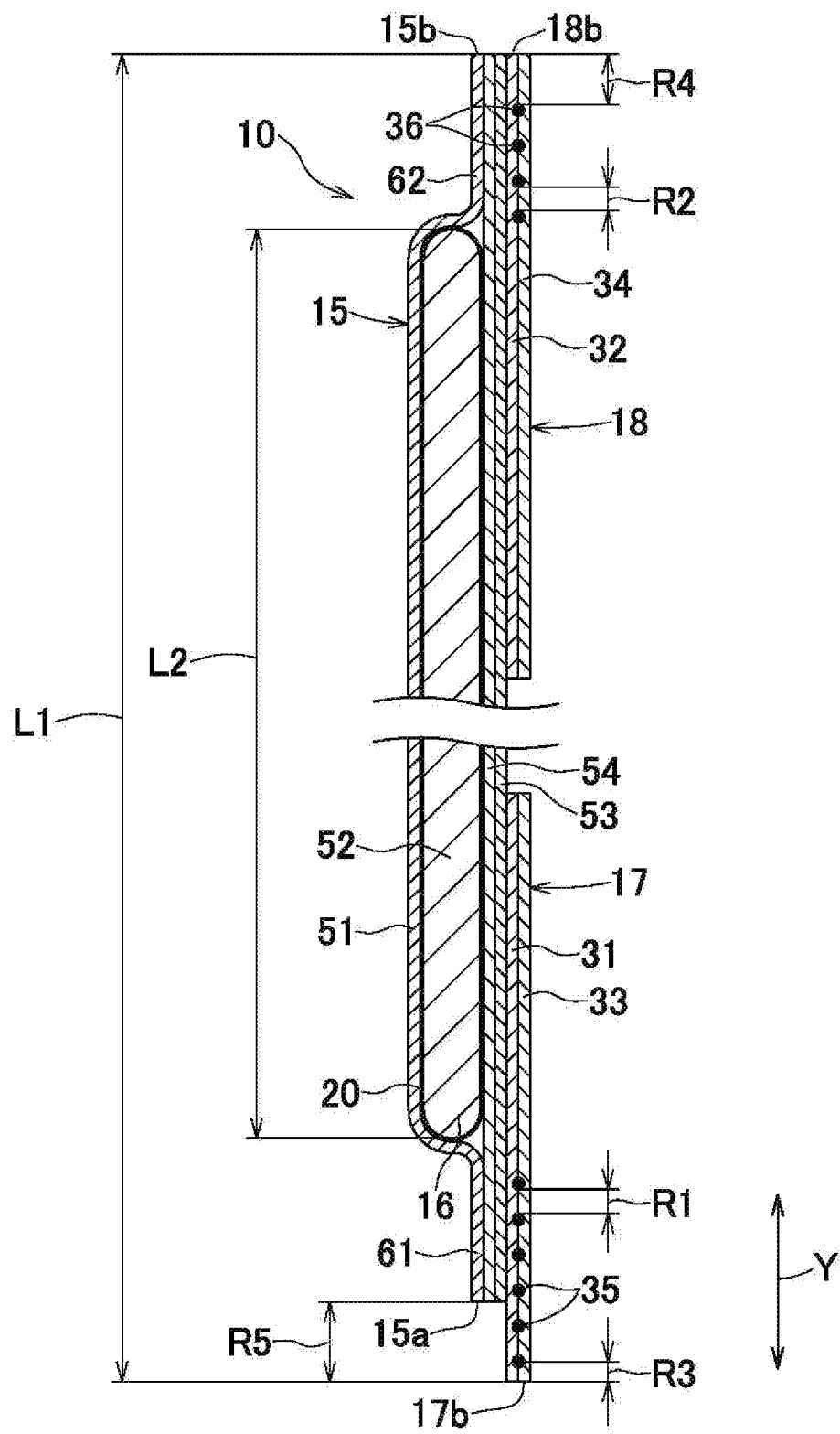
FIG. 3 is a schematic cross-sectional view taken along line III-III of FIG. 2.

Referring to FIGS. 2 and 3, the front and rear waist panels 17, 18 respectively include inner layer sheets 31, 32 on the skin facing surface, outer layer sheets 33, 34 on the non-skin facing surface, and waist elastics 35, 36 interposed between the inner and outer layer sheets 31, 32, 33, 34. The waist elastics 35, 36 extend in the lateral direction X and are contractibly secured in a stretchable state between the inner and outer layer sheets 31, 32, 33, 34 and include a front waist elastic 35 arranged in the front waist panel 17 and a rear waist elastic 36 arranged in the rear waist panel 18. The front and rear waist panels 17, 18 include front and rear waist elastic regions that are elastically contractible in the lateral direction X under the contraction action of the front and rear waist elastics 35, 36.

The inner layer sheets 31, 32 and the outer layer sheets 33, 34 have the same shape and size and form the exterior of the front and rear waist panels 17, 18, and have an oblong rectangular shape in the present embodiment. As the inner and outer layer sheets 31 to 34, for example, various known fibrous nonwoven fabrics whose basis mass per unit area ranges from about 10 to about 40 g/m2, which is liquid impermeable or hardly liquid-permeable, preferably moisture permeable, such as spunbonded fibrous nonwoven fabrics, meltblown fibrous nonwoven fabrics, SMS (spunbonded/meltblown/spunbonded) fibrous nonwoven fabrics, and air through fibrous nonwoven fabrics, can be used.

The front waist elastic region and the rear waist elastic region respectively include first elastic areas 41, 42 lying on the side of the waist opening and outboard of the liquid absorbent core 16 in the longitudinal direction Y, and second elastic areas 43, 44 lying on the side of the crotch region. The front and rear waist elastics 35, 36 disposed in the first elastic areas 41, 42 are continuously extended between the lateral edges 17*c*, 18*c* of the front and rear waist panels 17, 18. The second elastic areas 43, 44 are defined by a pair of elastic areas spacing apart from each other in the lateral direction X, and the front and rear waist elastics 35, 36 disposed in the pair of elastic areas extend from the lateral edges 17*c*, 18*c* of the front and rear waist panels 17, 18 to a lateral edge portion 16C of the liquid absorbent core 16.

Non-elastic areas, in which the front and rear waist elastics 35, 36 are not arranged, or even when the front and rear waist elastics 35, 36 are arranged, the contractile force thereof practically is not exerted, are positioned in an area overlapped with the central portion of the liquid absorbent core 16 in the lateral direction X, which is positioned between the pair of elastic areas defining the second elastic areas 43, 44. In addition to the instance in which the front and rear waist elastics 35, 36 constituting the elastic areas positioned on the lateral sides thereof are cut or removed, an instance is included which each non-elastic area is arranged in a mode in which its contractile force practically is not exerted. Thus, each elastic is arranged so as not to overlap the central portion of the liquid absorbent core 16, thereby suppressing the occurrence of gathers or deformation, which reduces the liquid absorption performance of the liquid absorbent core 16 by the contractile force of the elastics. Also, in a state of being worn, the central portion of the liquid absorbent core 16 may be expanded in the lateral direction X under the contraction action of the front and rear waist elastics 35, 36.

The front and rear waist elastics 35, 36 may be formed of string-like or strand-like elastic materials, whose fineness ranges from 300 to 1000 dtex, and are arranged in a state of being stretched about 1.8 to about 3.5 times. In the first elastic areas 41, 42, it is preferable that a spaced-apart dimension R1 between the front waist elastics 35 adjacent to each other in the longitudinal direction Y and a spaced-apart dimension R2 between the rear waist elastics 36 adjacent to each other in the longitudinal direction Y be respectively in a range of about 2 to about 8 mm. The terms "spaced-apart dimensions R1, R2" mean the distances of non-arrangement portions of the front and rear waist elastics 35, 36, which are positioned between the front and rear waist elastics 35, 36 adjacent to each other in the longitudinal direction Y. In the first elastic area 42, it is preferable that the plurality of rear waist elastics 36 be arranged with equal spaced-apart dimension R1 apart. In the present embodiment, in the first elastic areas 41, 42, the front and rear waist elastics 35, 36 are arranged at regular intervals apart in the longitudinal direction Y in such a manner that the spaced-apart dimension R1 of the front waist elastics 35 and the spaced-apart dimension R2 of the rear waist elastics 36 are respectively set to about 5 mm. It is noted that the spaced-apart dimensions of the front and rear waist elastics 35, 36 arranged in the first and second elastic areas 41, 42, 43, 44 in the longitudinal direction Y can be appropriately set, and for example, the spaced-apart dimensions may be set in such a manner as to be different in size with regard to the first elastic areas 41, 42 and the second elastic areas 43, 44. It is preferable that at least the rear waist elastics 36, out of the front and rear waist elastics 35, 36 arranged in the first elastic areas 41, 42, be respectively equal in terms of fineness and a stretch magnification ratio.

<Liquid Absorbent Structure>

Referring to FIG. 2, the liquid absorbent structure 15 has an approximately longitudinal rectangular shape and includes a front end edge 15a and a rear end edge (outer end edge) 15b extending in the lateral direction X and spaced apart from each other in the longitudinal direction Y, and lateral edges 15c extending in the longitudinal direction Y and spaced apart from each other in the lateral direction X, and includes a first portion 50A in the front waist region 11, a second portion 50B in the rear waist region 12, and a third portion 50C extending in the longitudinal direction Y between the first and second portions 50A, 50B and defining the crotch region 13. The first and second portions 50A, 50B are fixed on the inner surface of the front and rear waist panels 17, 18 through a joining region in which an adhesive means such as hot melt adhesives is applied.

Referring to FIGS. 2 to 5, the liquid absorbent structure 15 includes a liquid permeable bodyside liner 51, an absorbent body 52 in which the skin facing surface side is covered with the bodyside liner 51, and a hydrophobic outer sheet 53 beneath the bottom of the absorbent body 52. The absorbent body 52 includes the liquid absorbent core 16 formed of absorbent discrete materials such as fluff wood pulp and superabsorbent polymer particles, and a liquid permeable cover sheet 20, which is formed of tissue paper whose basis mass ranges from about 10 to about 20 g/m2, and that covers the whole of the liquid absorbent core.

The bodyside liner 51, for example, may be formed of hydrophilized spunbonded fibrous nonwoven fabrics, SMS fibrous nonwoven fabrics, and the like whose basis mass ranges from about 15 to about 25 g/m2. The outer sheet 53 is formed of hydrophobic SMS fibrous nonwoven fabrics, spunbonded nonwoven fabrics, and the like whose basis mass ranges from about 10 to about 25 g/m2. A liquid impermeable leakage-barrier sheet 54 formed of moisture permeable plastic films, whose basis mass ranges from about 10 to about 25 g/m2, is arranged between the outer sheet 53 and the absorbent body 52.

The outer sheet 53 has lateral edge portions extending outwardly from the lateral edges of the leakage-barrier sheet 54 in the lateral direction X. The lateral edge portion is inwardly folded (on the side of the absorbent body 52) along the folding line adjacent to the lateral edge of the leakage-barrier sheet 54 and extending in the longitudinal direction Y and has a proximal edge portion 55 fixed on the bodyside liner 51 and/or the leakage-barrier sheet 54 and forming a side flap, a front fixation end portion 56A and a rear fixation end portion 56B fixed on the skin facing surface of the bodyside liner 51 in the front and rear waist regions 11, 12, and a distal edge portion (free edge portion) 57 extending in the longitudinal direction Y between the front and rear fixation end portions 56A, 56B. A plurality of string-like or strand-like leg elastics 58 extending in the longitudinal direction Y are contractibly secured in a stretchable state between the outer sheets 53 placed at the proximal edge portion 55. The leg elastics 58 are arranged as to be spaced apart from each other in the lateral direction X, thereby defining a leg elastic area of a constant width.

The distal edge portion 57 has a sleeve formed by folding and fixing the outer lateral edge portion of the cover sheet 53, and a plurality of string-like or strand-like cuff elastics 59 extending in the longitudinal direction Y are contractibly secured in a stretchable state. When the diaper 10 is worn, the distal edge portion 57 are spaced away from the bodyside liner 51 toward the wearer under the contraction action of the cuff elastics 59, thereby forming a pair of leakage-barrier cuffs to prevent the lateral leakage of the body exudates. In the present embodiment, the front and rear fixation end portions 56A, 56B are folded and fixed to the outside of the lateral direction X along the fold 60 extended in the longitudinal direction Y, and the distal edge portion 57 has an inner lateral portion 57A between the fold 60 and the proximal edge portion 55, and an outer lateral portion 57B folded to the outside of the lateral direction X along the fold 60. The cuff elastics 59 are respectively arranged in the inner and outer lateral portions 57A, 57B of the distal edge portion 57. It is noted that, as long as the later-described effects of the present invention are achieved, the side flaps and the leakage-barrier cuffs may be formed with a pair of side sheets, which is a separate element from the outer sheets 53.

Referring to FIGS. 1 to 3, the rear end edge 15b (the outer end edge of a rear end portion 62) of the liquid absorbent structure 15 extends to the edge of the waist opening 21 and approximately aligns with the waist opening edge (that is, the outer end edge 18b of the rear waist panel 18) of the waist panel 14 in a plan view. The term "approximately align" means that errors in the process of manufacturing are included, and specifically means that a misalignment in the longitudinal direction Y between the waist opening edge of the waist panel 14 and the rear end edge 15b ranges within 5 mm. It is noted that, preferably, the rear end edge 15b and the waist opening edge of the waist panel 14 align with each other (that is, the misalignment is represented as 0 mm). In contrast, the front end edge 15a of the liquid absorbent structure 15 is positioned inboard of the waist opening edge of the waist panel 14 in the longitudinal direction Y.

Figure 4:
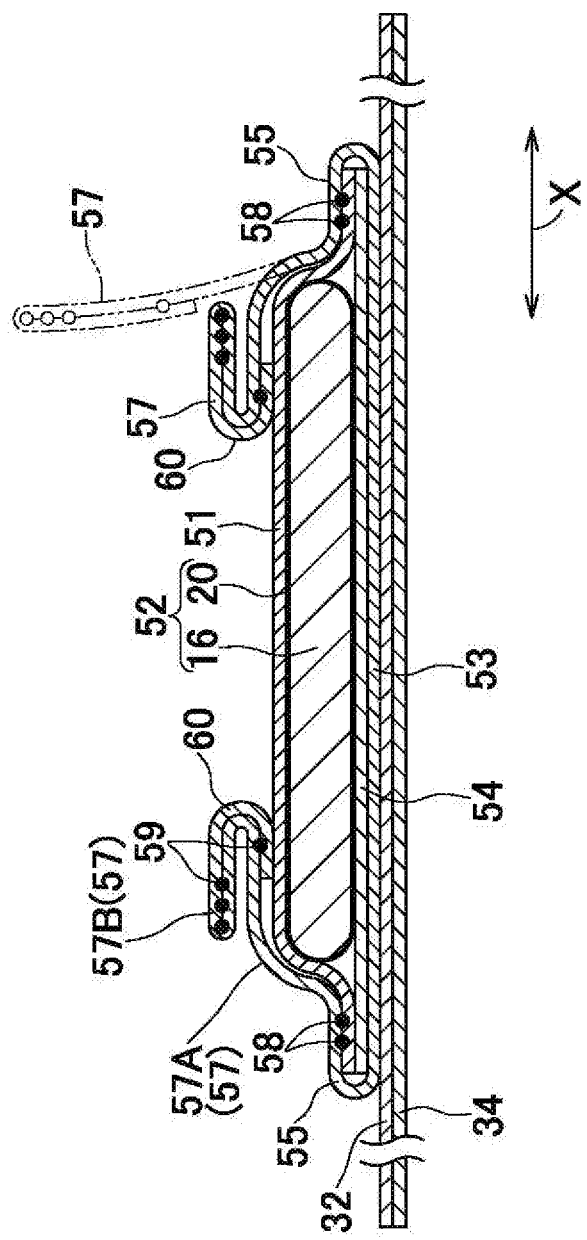
FIG. 4 is a schematic cross-sectional view taken along line IV-IV of FIG. 2.

Referring to FIGS. 2 to 4, in the liquid absorbent structure 15, a front end portion 61 and a rear end portion (end portion) 62 extending from the end edge of the liquid absorbent core 16 in the longitudinal direction Y to the outside of the core in the longitudinal direction Y are formed of a sheet member in which respective sheet materials (that is, the bodyside liner 51, the outer sheet 53, and the leakage-barrier sheet 54) are placed. Each sheet material has a longitudinally elongate rectangular shape having a constant width and extends from the front end edge 15a to the rear end edge 15b of the liquid absorbent structure 15. In the front and rear end portions 61, 62, the sheet member has equal folding stiffness (that is, stiffness with respect to the folding at which a fold extending in the lateral direction X is formed) in the longitudinal direction Y from the end edge of the liquid absorbent core 16 to the front and rear end edges 15a, 15b, and the folding stiffness up to the edge of the waist opening 21 in the longitudinal direction Y is equal in the rear end portion 62. Specifically, in the front and rear end portions 61, 62, the sheet member is such that thickness and basis mass per unit area are approximately equal (uniform) in the longitudinal direction Y.

Figure 6A:
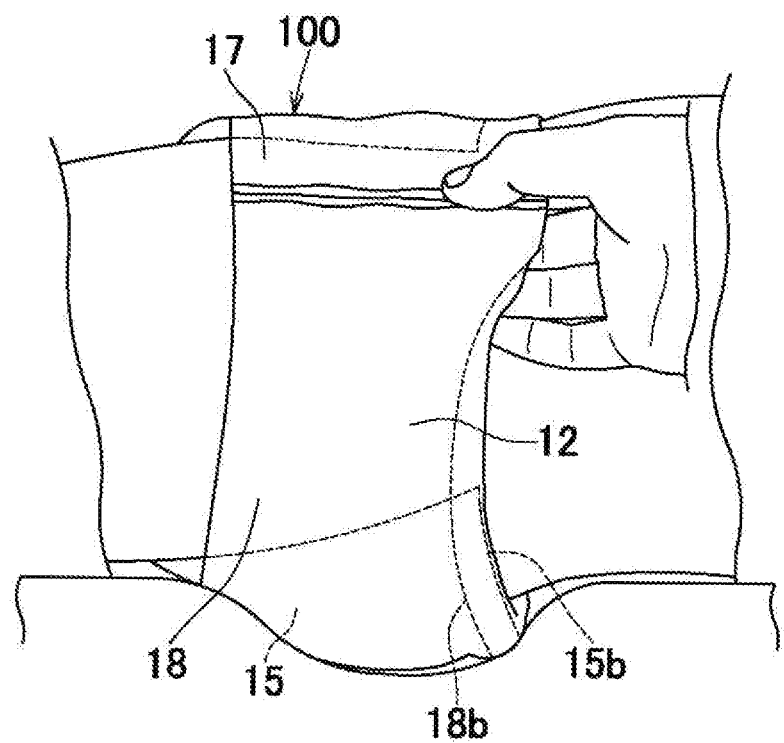
FIG. 6(*a*) is a view showing a situation during a putting-on operation of a conventional diaper, and FIG. 6(*b*) is a view showing a situation during the putting-on operation of the diaper of a first embodiment.

According to the diaper 10 described above, in the rear waist region 12, the waist panel 14 can be prevented from being folded in the longitudinal direction Y. Normally, in the pant-type diaper 10, a section in which stiffness in the longitudinal direction Y turns, specifically, a proximal edge of the section along which the end edge of the liquid absorbent core 16 extends in the lateral direction X is likely to define a guiding edge along which the waist panel 14 is folded in the longitudinal direction Y, but when the diaper 10 is pulled up, normally, the vicinity of the end edge of the liquid absorbent core 16 is held and raised with the fingers of a wearer or caretaker, and consequently the folding is suppressed by the fingers, and the folding does not occur in this section. However, when the section in which the guiding edge is defined in terms of folding in the longitudinal direction Y is present, outboard of the end edge of the liquid absorbent core 16 in the longitudinal direction Y, the waist panel 14 may be folded in the aforementioned section. Referring to FIG. 6(a), in a conventional pant-type diaper 100, when the diaper 100 is pulled up from a leg side to a torso side in order to put the diaper 100 on the wearer (infant) who is in a state of lying on his back, the rear end edge 15b of the liquid absorbent structure 15 is positioned inboard of the waist opening edge portion of the rear waist panel 18, and consequently the waist opening edge of the rear waist panel 18 having relatively low stiffness is easily folded on the inner surface side or outer surface side of the diaper 10 in a section where the rear end edge 15b is positioned, and when the waist opening edge portion of the rear waist panel 18 is folded on the inner surface side, the waist opening edge portion is interposed between the wearer's body and the inner surface of the liquid absorbent structure 15. In the aforementioned instance, a gap occurs between the folding section of the diaper 100 and the wearer's body, and body exudates may leak, and the central portion of the rear waist region 12 is positioned between the wearer's body and the bed, which brings a state where the wearer or caretaker has difficulty of visually recognizing the central portion, and the diaper 100 may be continuously worn while the folding goes unnoticed.

Figure 6B:
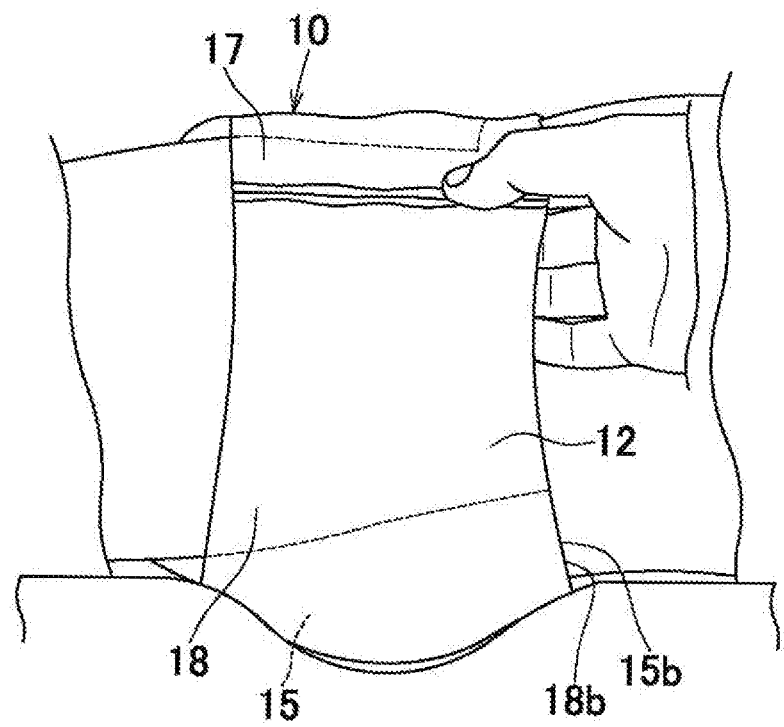

Referring to FIG. 6(b), in the diaper 10 of the present embodiment, the rear end edge 15b of the liquid absorbent structure 15 extends to the waist opening edge of the waist panel 14, so that the waist opening edge portion of the waist panel 14 is not folded along the rear end edge 15b, and when the wearer is lying on his back, the folding of the rear waist panel 18 is prevented, and whereby the leakage of body exudates are prevented. Also, it is not necessary to fix the folding of the rear waist region 12, which facilitates the wearing operation. Furthermore, as for the rear end portion 62 of the liquid absorbent structure 15, the number of sheet materials placed is large, and the rear end portion 62 has relatively high stiffness, compared with the rear waist panel 18, so that the folding can be reliably prevented on the outboard area of the liquid absorbent core 16 in the longitudinal direction Y where leakage is likely to occur.

Also, in the rear end portion 62 of the liquid absorbent structure 15, the folding stiffness in the longitudinal direction Y is equal up to the edge of the waist opening 21, and there is no section in which the stiffness turns in the longitudinal direction Y, and consequently there is no possibility that the sheet member is folded due to turning of the stiffness of the sheet member in the rear end portion 62. Furthermore, the number of sheet materials placed (that is, the inner and outer layer sheets 32, 34) that constitutes the waist panel 14 is equal from the rear end edge of the liquid absorbent core 16 to the waist opening edge in the longitudinal direction Y, and the folding stiffness of the sheet members constituting the waist panel 14 is approximately uniform in the longitudinal direction Y, so that there is no possibility that the waist panel 14 is folded in the longitudinal direction Y owing to turning in the stiffness of the sheet materials placed.

Referring to FIGS. 2, 5, as described above, the pair of leakage-barrier cuffs is positioned on the lateral edge portions of the liquid absorbent structure 15, and in the lateral edge portions 64 of the rear end portion 62 in the lateral direction X, the number of sheet materials placed is large, compared with a central portion 65 positioned therebetween, and the folding stiffness of the lateral edge portions in the longitudinal direction Y is higher than that of the central portion 65. Furthermore, the sheet materials (the outer sheet 53) forming the leakage-barrier cuffs are folded along the folding line 60 and placed, and the folding stiffness thereof is high. Thus, in the lateral edge portions 64, the number of sheet materials placed is increased, and basis mass per unit area is increased, so that the folding stiffness with respect to the longitudinal direction Y is enhanced, and the folding in the longitudinal direction Y in the rear end portion 62 is further suppressed, and a pleasant touch can be favorably maintained by means of the soft sheet member having relatively low stiffness in the central portion 65. Also, as is the same with the rear end portion 62, as for the lateral edge portions 64 of the front end portion 61 in the lateral direction X, the folding stiffness in the longitudinal direction Y is high, compared with the central portion 65.

In the present embodiment, the front and rear fixation end portions 56A and 56B of the leakage-barrier cuffs are positioned on the lateral edge portions 64 of the front and rear end portions 61, 62 of the liquid absorbent structure 15. Specifically, respective inner end edges of the front fixation end portion 56A and the rear fixation end portion 56B of the leakage-barrier cuffs in the longitudinal direction Y are overlapped with the liquid absorbent core 16 in a plan view, and respective outer end edges align with respective front and rear end edges 15a, 15b of the liquid absorbent structure 15. In the front and rear fixation end portions 56A and 56B, the sheet materials forming the leakage-barrier cuffs are hardened by applying an adhesive coating or the like, which increases the folding stiffness. Also, in the aforementioned diaper 10, the front and rear fixation end portions 56A, 56B having relatively high stiffness are positioned on the outboard area of the liquid absorbent core 16 in the longitudinal direction Y and on the lateral sides in the lateral direction X, so that the area of the absorbent body 52 is prevented from being practically reduced by the contraction action of the front and rear waist elastics 35, 36, thereby making effective use of the absorption area of the absorbent body 52.

Referring to FIG. 1, in the region in which the rear end portion 62 of the liquid absorbent structure 15 is positioned, the first elastic area 42 that is contractible in the lateral direction X is formed in the rear waist panel 18, and a plurality of gathers (creases) 66 extending in the longitudinal direction Y are formed under the contraction action of the rear waist elastic 36 in the sheet members forming the rear end portion 62 and the rear waist panel 18. The gathers 66 as described above are formed when the diaper 10 is worn, so that basis mass per unit area is increased, and the folding stiffness in the longitudinal direction Y is increased, and the effects of preventing the folding are improved. Also, in the first elastic area 42, the spaced-apart dimension of the rear waist elastic 36 is equal to or less than about 8 mm, which is relatively small, so that the folding of the sheet member positioned in the rear end portion 62 can be further suppressed. Furthermore, in the present embodiment, the spaced-apart dimensions R2 (pitches) of the rear waist elastics 36 adjacent to each other are equal, so that the fiber density of the sheet member is approximately uniformly increased in the longitudinal direction Y, and the section, which defines a guiding edge of the folding in the longitudinal direction Y, is hardly formed. It is noted that, in the rear waist region 12, it is preferable that the rear waist elastics 36 be arranged in such a manner as to be spaced apart from the waist opening edge with about 1 to about 10 mm apart.

Referring to FIGS. 2 and 3, in the front waist region 11, the front end edge 15*a* of the liquid absorbent structure 15 is spaced apart in such a manner as to be positioned inboard of the waist opening edge, which enhances the flexibility of the waist opening edge portion of the front waist panel 17 and makes it easy to deform the waist opening edge portion in accordance with the roundness of an abdominal region. In the front waist region 11, the front waist elastic 35 nearest to the side of the waist opening 21 is positioned outboard of the front end portion 61 of the liquid absorbent structure 15 in the longitudinal direction Y. Also, a spaced-apart dimension R3 between the front waist elastic 35 nearest to the side of the waist opening 21 and the waist opening edge is smaller than a spaced-apart dimension R4 between the rear waist elastic 36 nearest to the side of the waist opening 21 in the rear waist region 12 and the waist opening edge. Furthermore, in the present embodiment, a spaced-apart dimension R5 in the longitudinal direction Y between the front end edge 15*a* of the liquid absorbent structure 15 and the waist opening edge (the outer end edge 17*b* of the front waist panel 17) is equal to or less than about 20 mm.

Referring to FIG. 3, the size L2 of the liquid absorbent core 16 in the longitudinal direction Y is about 70 percent or higher than the size L1 of the diaper 10 in the longitudinal direction Y, preferably, about 75 to about 85 percent of the size L1 of the diaper 10. Normally, the size of the liquid absorbent core in the longitudinal direction is about 60 percent of the size of a diaper in the longitudinal direction, and in the diaper 10 of the present embodiment, the area formed only with the sheet member positioned outboard of the liquid absorbent core in the longitudinal direction is relatively expanded. In the present embodiment, the size L2 of the liquid absorbent core 16 is relatively extended, and the size of the length of an area, which is made up of only the sheet member positioned outboard of the liquid absorbent core 16 in the longitudinal direction Y, is reduced, thereby further suppressing the occurrence of the folding. The diaper 10 described above is suitable for the relatively small-size diaper 10 for infants, in which the size L1 in the longitudinal direction Y is about 290 to about 420 mm. Referring to FIG. 3, in the present embodiment, in the front and rear waist regions 11, 12, the spaced-apart dimensions in the longitudinal direction Y from the waist opening edge to the end edge of the liquid absorbent core 16 are approximately equal.

Figure 7:
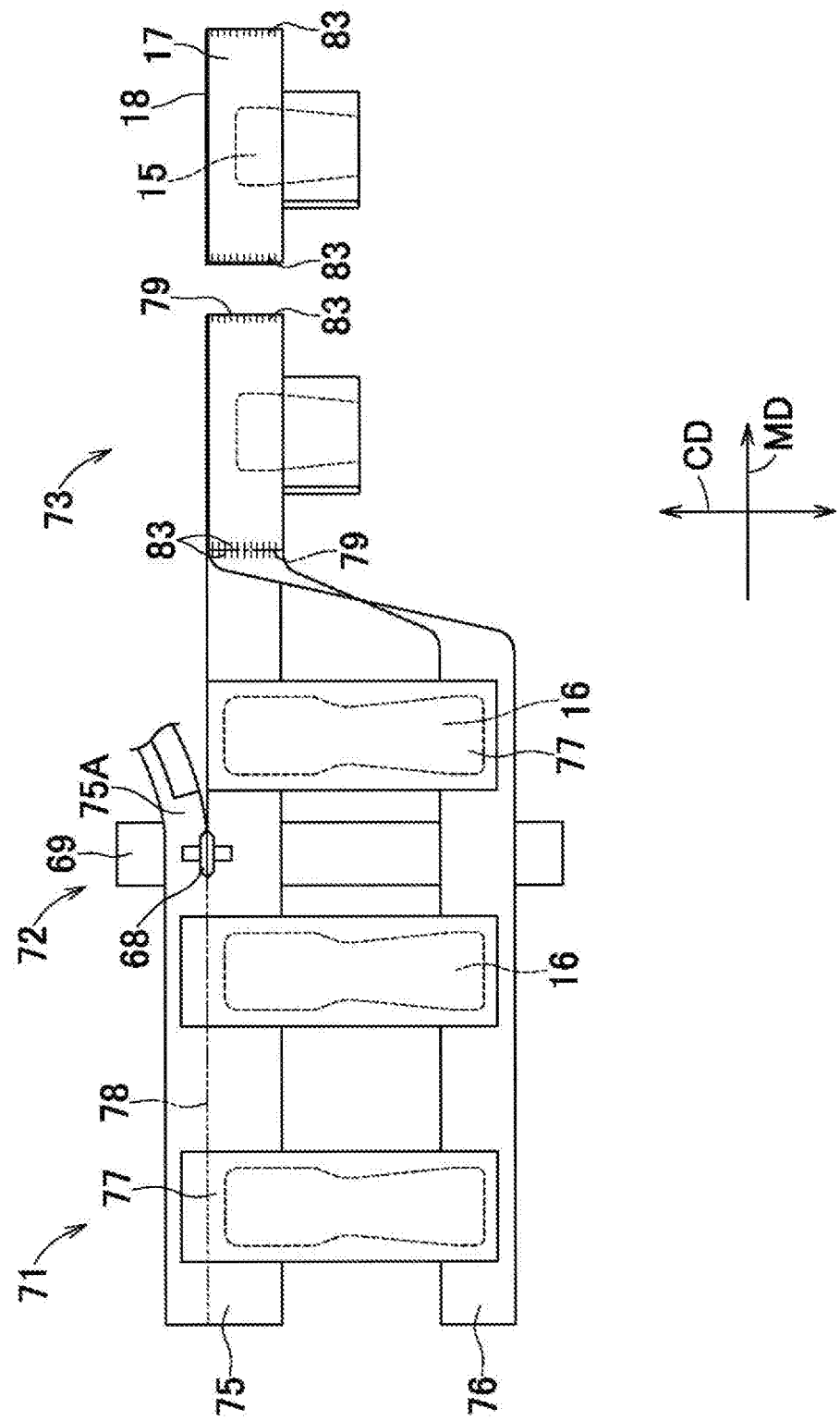
FIG. 7 is a view showing part of manufacturing processes as one example of a manufacturing method of the diaper.

FIG. 7 is a view showing one example of the manufacturing method of the diaper 10 and shows part of manufacturing processes of the diaper 10. In a first process 71 of the manufacturing processes, a first continuous panel 75, which serves as a base material of the rear waist panel 18, and a second continuous panel 76, which serves as a base material of the front waist panel 17, are continuously transferred in a mechanical direction MD in a state of being arranged in parallel to each other by means of transfer rollers not shown. A liquid absorbent panel 77, which serves as a base material of the liquid absorbent structure 15, is intermittently arranged on one surface of the first and second continuous panels 75, 76 in the mechanical direction MD, thereby forming a composite panel, which serves a base material of diaper 10. The lateral end portions of the liquid absorbent panel 77 are respectively joined with the first continuous panel 75 and the second continuous panel 76 through a joining means such as a hot melt adhesive.

In a second process 72, the outer lateral edge portion 75A of the first continuous panel 75 and the end portion of the liquid absorbent panel 77 placed on the continuous panel 75 are cut with a cutting device including a rotary blade 68. The first continuous panel 75 and the liquid absorbent panel 77 are transferred between the rotary blade 68 and a driven roller 69 arranged opposite to the rotary blade 68 and cut along a cutting line 78 extending along the mechanical direction MD. The cutting line 78 is in a non-arrangement region of the liquid absorbent core 16 in the first continuous panel 75 and set at a position overlapped with the end portion of the liquid absorbent panel 77. The outer lateral edge of the second continuous panel and the end edge of the liquid absorbent panel 77, which is formed by the cutting line 78, correspond to each other in a plan view. In a third process 73, after the composite panel is folded in two in such a manner that the liquid absorbent panel 77 is disposed on the inner side, sealing treatment is applied between the liquid absorbent panels (the liquid absorbent structure 15) 77 adjacent to each other, and a pair of joining portions 83 extended in a cross-direction CD (the direction orthogonal to the mechanical direction MD) is formed. The composite panel is cut between the pair of joining portions 83 along a cutting line 79 extending in the intersecting direction CD, and an individual diaper 10 is formed. According to the aforementioned manufacturing method, the rear end edge 15*b* of the liquid absorbent structure 15 and the outer end edge 18*b* (the waist opening edge) of the rear waist panel 18 can be easily aligned with each other.

Figure 8:
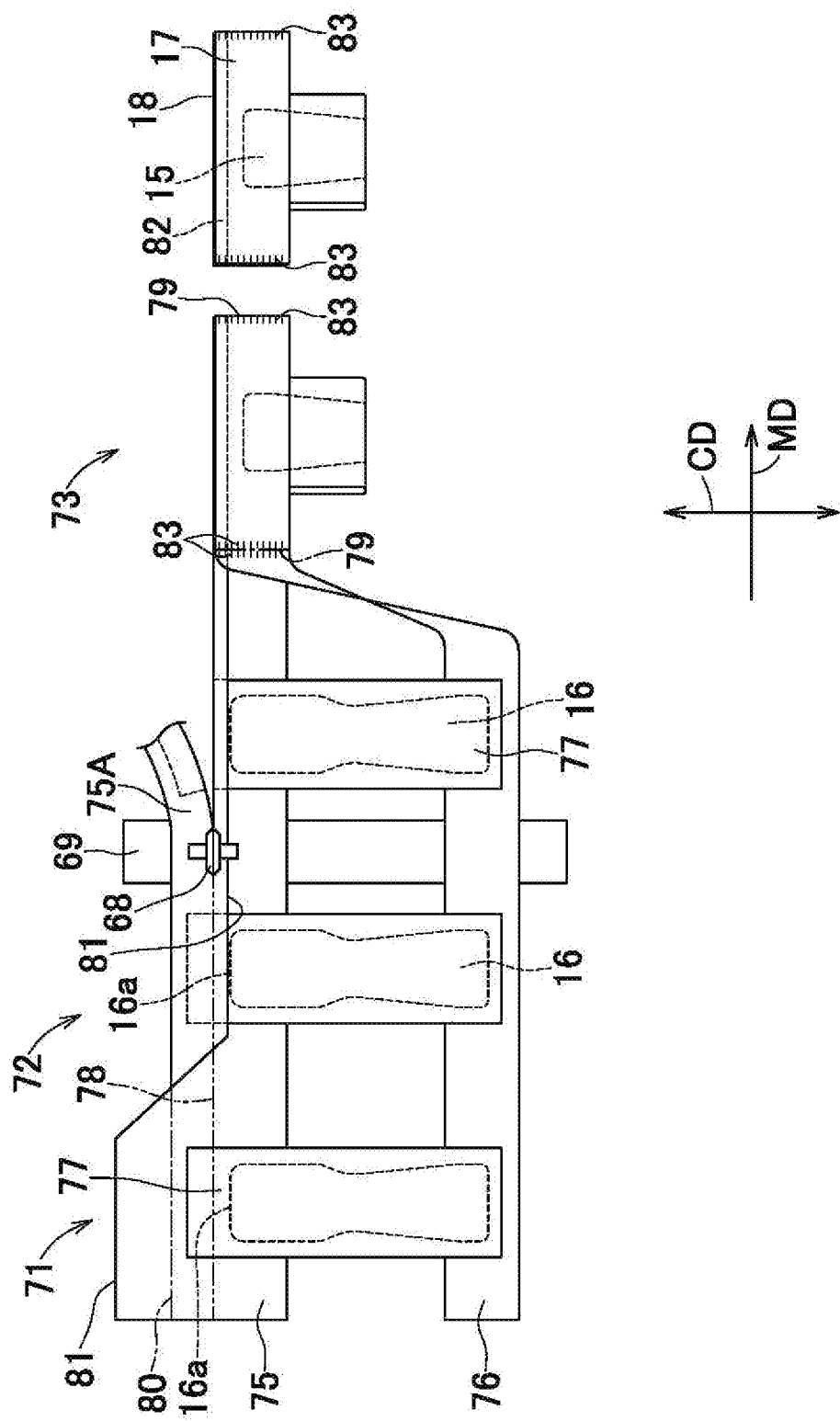
FIG. 8 is a view showing part of manufacturing processes as another example of the manufacturing method of the diaper.

It is noted that, as another example of the manufacturing method shown in FIG. 8, in the second process 72, after the outer lateral portion of the first continuous panel 75 is folded on the inner surface side (the surface side where the liquid absorbent panel 77 is arranged) along a folding line 80 extending in the mechanical direction MD, the outer lateral edge portion 75A of the first continuous panel 75 and the end portion of the liquid absorbent panel 77 may be cut with the rotary blade 68. It is preferable that the folding line 80 be positioned outboard of the end edge of the liquid absorbent panel 77 in the crossing direction CD so as not to overlap the end portion of the liquid absorbent panel 77, and it is preferable that part of the folding section of the first continuous panel 75 be placed on the end edge of the liquid absorbent panel 77. Also, it is preferable that an outer lateral edge 81 of the first continuous panel 75 be positioned in the vicinity of the end edge 16a of the liquid absorbent core 16 (specifically, in a range within about 10 mm from the end edge 16a of the liquid absorbent core 16 in the cross-direction CD) in a state after being folded along the folding line 80. The diaper 10 formed by the aforementioned manufacturing method is provided as the diaper 10 in which an auxiliary sheet 82 extending in the lateral direction X on the inner surface side of the rear end portion 62 of the liquid absorbent structure 15 is placed as an option in the rear waist panel 18. It is noted that, although not shown, in the second process, as is the same with the first continuous panel 75, the outer lateral portion of the second continuous panel 76 is folded, and the auxiliary sheet may be arranged on the inner surface side of the front end portion 61 of the liquid absorbent structure 15 in the front waist panel 17 of the diaper 10.

It is noted that in the diaper 10, the end edge of at least one end portion out of the front and rear end portions 61, 62 of the liquid absorbent structure 15 only needs to extend to the waist opening edge of the waist panel 14, and for example, constitution in which only the front end portion 61 of the liquid absorbent structure 15 extends to the waist opening edge of the front waist panel 17 may be applied, or constitution in which both of the front and rear end portions 61, 62 respectively extend to the waist opening edges of the front and rear waist panels 17, 18 may be applied. When the front and rear end edges 15a, 15b of the liquid absorbent structure 15 respectively extend to the waist opening edges, and the diaper 10 is similarly pulled up on the side of the front waist region 11, the waist opening edge portion is not prone to be folded, which facilitates the putting-on operation.

When the end edges (the front and rear end edges 15a, 15b) of the liquid absorbent structure 15 in both of the front and rear waist regions 11, 12 are fitted to the waist opening edges of the waist panel 14, the cutting line 78 extending in the mechanical direction MD is set in both the first and second continuous panels 75, 76, in such a manner as to overlap the end portion of the liquid absorbent panel 77, and the outer lateral edges of the first and second continuous panels 75, 76 only need to be cut. In the aforementioned manufacturing method, the position of the cutting line 78 forming the waist opening is appropriately set, which makes it possible to easily change the sizes of the front and rear waist regions 11, 12 in the longitudinal direction Y, and the small-size diaper 10 (the size L1 in the longitudinal direction Y is small) can be easily manufactured by increasing a cutting width.

Second Embodiment

Figure 9:
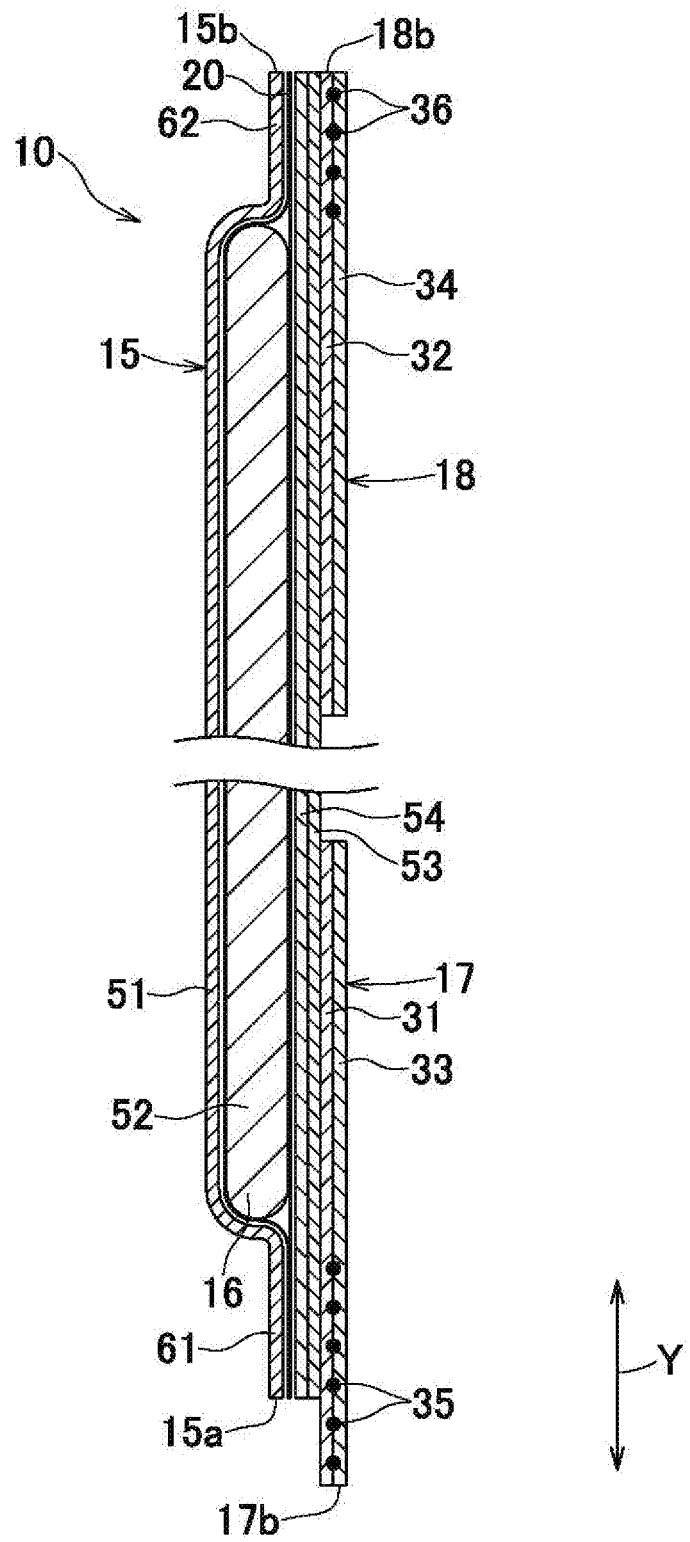
FIG. 9 is a view similar to FIG. 3 showing the diaper of a second embodiment.

FIG. 9 is a view similar to the diaper 10 shown in FIG. 3 according to a second embodiment. The basic constitution of the diaper 10 according to the present embodiment is similar to that of the first embodiment, and accordingly, only a point of difference will be described below.

In the diaper 10 according to the second embodiment, the cover sheet 20 for the liquid absorbent core 16 extends from the front end edge 15a to the rear end edge 15b of the liquid absorbent structure 15. The cover sheet 20 is formed in a longitudinal rectangular shape having a uniform width size in a plan view. In the aforementioned diaper 10, the cover sheet 20 is placed in the rear end portion 62, thereby further increasing the folding stiffness of the sheet member of the rear end portion 62 in the longitudinal direction Y.

It is noted that, in each embodiment, the waist panel 14 is formed in an annular shape, but the shape of the waist panel 14 is not limited to this. For example, in the front and rear waist regions 11, 12, the central portion in the lateral direction X may be separated and formed with a pair of side panels arranged on both sides of the liquid absorbent structure 15, and in the aforementioned diaper 10, at least the end edge of one end portion out of the front and rear end portions 61, 62 of the liquid absorbent structure 15 extends to the waist opening edge in such a manner as to approximately align with the waist opening edge of the waist panel (side panel) 14 in a plan view.

Besides the materials described in the description, various known materials, which are normally used in the field of this sort, may be used for each constitution member constituting the disposable diaper 10 of the present invention without restriction. Also, in the description and claims, the terms "first" and "second" are merely used to distinguish similar elements and positions.

The invention claimed is:

1. A disposable wearing article, comprising:
    a longitudinal direction and a lateral direction,
    front and rear waist regions,
    a crotch region extending between the front and rear waist regions,
    a waist panel for forming the front and rear waist regions,
    a liquid absorbent structure that extends from the crotch region to the front and rear waist regions and includes a liquid absorbent core,
    a waist opening, and
    a pair of leg openings, wherein
    the liquid absorbent structure includes
        a rear end portion extending from a rear end edge of the liquid absorbent core to a side of the waist opening in the rear waist region, and
        a front end portion extending from a front end edge of the liquid absorbent structure to a side of the waist opening in the front waist region,
    in the rear waist region, a waist opening edge of the waist panel and an outer end edge of the rear end portion of the absorbent structure overlap each other in a plan view,
    in the front waist region, the waist opening edge of the waist panel and an outer end edge of the front end portion of the absorbent structure are spaced apart from each other in the longitudinal direction in a range of 5-20 mm,
    the front and rear end portions of the liquid absorbent structure include both lateral edge portions spaced apart from each other in the lateral direction and a central portion between both the lateral edge portions, and both the lateral edge portions have higher folding stiffness in the longitudinal direction than the central portion,
    the waist panel includes
        inner layer sheets configured to face a wearer's skin when the disposable wearing article is worn,
        outer layer sheets configured to face away from the wearer's skin when the disposable wearing article is worn, and
        front and rear waist elastics interposed between the inner and outer layer sheets, and
    a first spaced-apart dimension between the waist opening edge and one of the front waist elastics nearest to the waist opening is smaller than a second spaced-apart dimension between the waist opening edge and one of the rear waist elastics nearest to the waist opening.

2. The wearing article according to claim 1, wherein at least in a region overlapped with the front and rear end portions of the liquid absorbent structure in the plan view, a folding stiffness of a sheet member constituting the waist panel in the longitudinal direction is uniform.

3. The wearing article according to claim 1, wherein in a region overlapped with the front and rear end portions of the liquid absorbent structure in the plan view, the waist panel is contractible in the lateral direction.

4. The wearing article according to claim 3,
wherein the front and rear waist elastics are string-shaped or strand-shaped waist elastics extending in the lateral direction, and
wherein in the region overlapped with the front and rear end portions of the liquid absorbent structure in the plan view, spaced-apart distances between the front waist elastics adjacent to each other in the longitudinal direction are equal, and spaced-apart distances between the rear waist elastics adjacent to each other in the longitudinal direction are equal.

5. The wearing article according to claim 1,
wherein the liquid absorbent structure includes a pair of leakage-barrier cuffs positioned on lateral sides in the lateral direction and on a skin facing surface side of the liquid absorbent core, and
wherein the pair of leakage-barrier cuffs includes a fixation end portion extending from the end edge of the liquid absorbent core to an edge of the waist opening in the front and rear waist regions.

6. The wearing article according to claim 1,
wherein the liquid absorbent structure includes a cover sheet for the liquid absorbent core, and
wherein the cover sheet extends to the edge of the waist opening in the front and rear waist regions.

\* \* \* \* \*